(12) United States Patent
Choi et al.

(10) Patent No.: US 12,266,441 B2
(45) Date of Patent: Apr. 1, 2025

(54) IMPLANT SURGERY PLANNING METHOD USING AUTOMATIC PLACEMENT OF IMPLANT STRUCTURE, USER INTERFACE PROVIDING METHOD THEREFOR, AND TEETH IMAGE PROCESSING DEVICE THEREFOR

(71) Applicant: Osstem Implant Co., Ltd., Seoul (KR)

(72) Inventors: Kyoo Ok Choi, Seoul (KR); Eung Jun Lee, Gyeonggi-do (KR); Hyun Suk Kim, Gyeonggi-do (KR)

(73) Assignee: Osstem Implant Co., Ltd., Seoul (KR)

( * ) Notice: Subject to any disclaimer, the term of this patent is extended or adjusted under 35 U.S.C. 154(b) by 582 days.

(21) Appl. No.: 17/623,815

(22) PCT Filed: May 11, 2020

(86) PCT No.: PCT/KR2020/006138
§ 371 (c)(1),
(2) Date: Dec. 29, 2021

(87) PCT Pub. No.: WO2021/006471
PCT Pub. Date: Jan. 14, 2021

(65) Prior Publication Data
US 2022/0246269 A1 Aug. 4, 2022

(30) Foreign Application Priority Data

Jul. 11, 2019 (KR) ........................ 10-2019-0083833

(51) Int. Cl.
*G06T 7/11* (2017.01)
*A61B 34/00* (2016.01)
(Continued)

(52) U.S. Cl.
CPC ............. *G16H 20/40* (2018.01); *A61B 34/10* (2016.02); *A61B 34/25* (2016.02); *G06T 7/0012* (2013.01);
(Continued)

(58) Field of Classification Search
CPC ........ G16H 20/40; A61B 34/10; A61B 34/25; A61B 2034/102; A61B 2034/105;
(Continued)

(56) References Cited

U.S. PATENT DOCUMENTS 8,021,147 B2 * 9/2011 Sporbert .............. A61C 9/0046
433/24
10,695,150 B2 * 6/2020 Kopelman ........... G06V 10/758
(Continued)

FOREIGN PATENT DOCUMENTS

CN 105662618 A 6/2016
KR 10-2011-0132825 A 12/2011
(Continued)

*Primary Examiner* — Vijay Shankar
(74) *Attorney, Agent, or Firm* — Downs Rachlin Martin PLLC

(57) ABSTRACT

Disclosed are an implant surgery planning method using automatic placement of an implant structure, a user interface providing method therefor, and a teeth image processing device therefor. One embodiment provides an implant surgery planning method using automatic placement of an implant structure, a user interface providing method therefor, and a teeth image processing device therefor, wherein during planning, placement of an implant structure is automatically performed with respect to all missing-tooth areas as well as a single missing-tooth area in a teeth image, and placement of an implant structure is automatically performed on the basis of information on relation with a surrounding structure of the missing-tooth area, whereby the present invention increases a user's convenience.

15 Claims, 7 Drawing Sheets

(51) Int. Cl.
*A61B 34/10* (2016.01)
*G06T 7/00* (2017.01)
*G06T 7/62* (2017.01)
*G06T 7/70* (2017.01)
*G06T 11/00* (2006.01)
*G16H 20/40* (2018.01)

(52) U.S. Cl.
CPC ................. *G06T 7/11* (2017.01); *G06T 7/62* (2017.01); *G06T 7/70* (2017.01); *G06T 11/00* (2013.01); *A61B 2034/102* (2016.02); *A61B 2034/105* (2016.02); *A61B 2034/108* (2016.02); *G06T 2200/24* (2013.01); *G06T 2207/30036* (2013.01); *G06T 2207/30052* (2013.01)

(58) Field of Classification Search
CPC ..... A61B 2034/108; A61B 6/51; A61B 6/463; A61B 6/5211; A61B 6/5294; A61B 2034/107; A61B 6/5217; A61B 6/5229; A61B 2034/101; G06T 7/0012; G06T 7/11; G06T 7/62; G06T 7/70; G06T 11/00; G06T 2200/24; G06T 2207/30036; G06T 2207/30052; A61C 1/084; A61C 5/77; A61C 13/0004; A61C 8/0089
See application file for complete search history.

(56) References Cited

U.S. PATENT DOCUMENTS

| | | |
|---|---|---|
| 2007/0264612 A1 | 11/2007 | Mount |
| 2009/0162813 A1 | 6/2009 | Glor et al. |
| 2014/0278279 A1 | 9/2014 | Azernikov et al. |
| 2018/0168781 A1* | 6/2018 | Kopelman ............. A61B 34/10 |
| 2018/0311019 A1* | 11/2018 | Kim ................... A61C 13/0004 |
| 2021/0306599 A1* | 9/2021 | Pierce .................... A61B 90/35 |
| 2022/0168044 A1* | 6/2022 | Oliveira ................ G06T 7/0012 |
| 2023/0390031 A1* | 12/2023 | Marshall ............... G16H 50/70 |

FOREIGN PATENT DOCUMENTS

| | | |
|---|---|---|
| KR | 10-2017-0077785 A | 7/2017 |
| KR | 101888361 | 9/2018 |
| KR | 10-2018-0120890 A | 11/2018 |
| KR | 20180136659 A | 12/2018 |
| KR | 101917140 | 1/2019 |
| KR | 10-2019-0037807 A | 4/2019 |
| KR | 10-2019-0065590 A | 6/2019 |
| WO | 2012-004937 A1 | 1/2012 |

* cited by examiner

IMPLANT SURGERY PLANNING METHOD USING AUTOMATIC PLACEMENT OF IMPLANT STRUCTURE, USER INTERFACE PROVIDING METHOD THEREFOR, AND TEETH IMAGE PROCESSING DEVICE THEREFOR

CROSS-REFERENCES TO RELATED APPLICATIONS

This application is a U.S. national phase application, pursuant to 35 U.S.C. § 371, of PCT/KR2020/006138, filed May 11, 2020, designating the United States, which claims priority to Korean Application No. 10-2019-0083833, filed Jul. 11, 2019. The entire contents of the aforementioned patent applications are incorporated herein by this reference.

TECHNICAL FIELD

The following description relates to a medical image processing technology including a guide design technology for dental implant surgery.

Background Art

An implant surgery process using software is a process of planning the placement of implant structures (crowns, abutments, fixtures, and the like) on the software prior to implant surgery, and virtually placing the implant structures on a teeth image. The implant placement planning process requires a lot of manual operations of a user. For example, in determining a position of a fixture, a final position of the fixture is determined as the user manually makes an adjustment through multiple click operations after an initial fixture placement position is determined. As such, general software requires many clicks and a complicated user operation for the placement of the implant structures.

DISCLOSURE OF THE INVENTION

Technical Goals

An aspect provides an implant surgery planning method that minimizes manual operations of a user and is convenient, a user interface providing method therefor, and a teeth image processing device therefor.

Technical Solutions

According to an aspect, there is provided an implant surgery planning method including entering a predetermined automatic placement mode, with respect to a teeth image, among a single placement mode for automatically placing an implant structure with respect to a single missing-tooth area in the teeth image, and a multiple placement mode for automatically placing the implant structure with respect to all missing-tooth areas in the teeth image, recognizing at least one missing-tooth area through tooth segmentation in the entered automatic placement mode, analyzing information on a relation with a surrounding structure on the basis of the recognized missing-tooth area, and automatically placing the implant structure in the at least one missing-tooth area by reflecting the analyzed information on the relation with the surrounding structure.

The entering of the predetermined automatic placement mode may include entering a single placement mode by receiving a selection signal for designating a predetermined missing-tooth area in the teeth image, and entering a multiple placement mode by receiving the selection signal through a user interface for automatically placing implant structures with respect to all missing teeth in the teeth image.

The recognizing of the at least one missing-tooth area may include removing a bone part from the teeth image, segmenting a tooth area in the teeth image from which the bone part is removed, designating a tooth number to the segmented tooth area along a preset axial direction, and extracting the at least one missing-tooth area from the tooth area designated with the tooth number.

The automatically placing of the implant structure may include determining a diameter of a fixture according to a designated tooth number, determining a length of the fixture by reflecting a length of an adjacent tooth on the basis of the missing-tooth area, determining an angle including an inclination of the fixture so as to be parallel to the adjacent tooth in a mesial direction on the basis of the missing-tooth area, and determining a position of the fixture so that at least one of a distance to a gingival bone, a distance to a cortical bone, a distance to the adjacent tooth, and a distance between adjacent fixtures is a preset interval.

The automatically placing of the implant structure may include disposing a crown at a predetermined distance on the basis of an upper end of a fixture whose position is determined, determining a width of the crown according to a space of a missing-tooth area between adjacent teeth, determining a height of the crown according to an occlusal height of an antagonist tooth, and determining the height of the crown in a ratio of other teeth when there is one or no adjacent tooth.

The implant surgery planning method may further include simultaneously performing simulations for a plurality of crowns.

The simultaneously performing of the simulations for the plurality of crowns may include automatically generating a bridge according to the number of fixtures placed, and generating a bridge that connects crowns successively placed at positions corresponding to those of respective fixtures when a middle fixture is deleted in a state in which three or more fixtures are successively placed in the teeth image.

According to another aspect, there is provided a user interface providing method for implant surgery planning, the method including displaying a teeth image, displaying a user interface for placing an implant structure with respect to all missing teeth in the teeth image, entering a single placement mode when a selection signal for designating a predetermined missing-tooth area in the teeth image is received, automatically placing the implant structure in the designated missing-tooth area, and displaying the placed implant structure on a screen, and entering a multiple placement mode when a selection signal for the user interface is received, automatically placing the implant structure in all missing-tooth areas, and displaying the placed implant structure on the screen.

According to still another aspect, there is provided a teeth image processing device including a data acquisition unit configured to acquire teeth image data, a controller configured to automatically place and simulate an implant structure in at least one missing-tooth area by configuring a screen for performing a single placement mode and a multiple placement mode with respect to an acquired teeth image, analyzing information on a relation with a surrounding structure on the basis of the missing-tooth area, and reflecting the analyzed information on the relation with the surrounding structure, an input unit configured to receive an operation signal for entering a predetermined automatic placement mode, and an output unit configured to display an automatic placement mode screen, and display a placement result on the teeth image.

The output unit may be configured to display a user interface for entering the multiple placement mode on the screen, and the controller may be configured to enter the single placement mode when a selection signal for designating a predetermined mis sing-tooth area in the teeth image is received from the input unit, and automatically place the implant structure in the designated missing-tooth area, and enter the multiple placement mode when a selection signal for the user interface for entering the multiple placement mode is received from the input unit, and automatically place the implant structure in all missing-tooth areas.

The controller may be configured to perform image processing to remove a bone part from the teeth image and segment a tooth area in the teeth image from which the bone part is removed, designate a tooth number to the segmented tooth area along a preset axial direction, and extract at least one missing-tooth area from the tooth area designated with the tooth number.

The controller may be configured to determine a diameter of a fixture according to a designated tooth number, determine a length of the fixture by reflecting a length of an adjacent tooth on the basis of the missing-tooth area, determine an angle including an inclination of the fixture so as to be parallel to the adjacent tooth in a mesial direction on the basis of the missing-tooth area, and determine a position of the fixture so that at least one of a distance to a gingival bone, a distance to a cortical bone, a distance to the adjacent tooth, and a distance between adjacent fixtures is a preset interval.

The controller may be configured to dispose a crown at a predetermined distance on the basis of an upper end of a fixture whose position is determined, determine a width of the crown according to a space of a missing-tooth area between adjacent teeth, determine a height of the crown according to an occlusal height of an antagonist tooth, and determine the height of the crown in a ratio of other teeth when there is one or no adjacent tooth.

The controller may be configured to simultaneously perform simulations for a plurality of crowns. The controller may be configured to automatically generate a bridge according to the number of fixtures placed, and generate a bridge that connects crowns successively placed at positions corresponding to those of respective fixtures when a middle fixture is deleted in a state in which three or more fixtures are successively placed in the teeth image.

Advantageous Effects

According to an implant surgery planning method using automatic placement of an implant structure, a user interface providing method therefor, and a teeth image processing device therefor according to aspects, a user's convenience may be increased by minimizing manual operations of the user when a virtual implant structure is placed on a teeth image.

For example, as a missing-tooth area is automatically extracted through tooth segmentation, an implant structure may be automatically placed in all missing-tooth areas even when a user does not move to every single missing-tooth area and designate the missing-tooth area. The placement of the implant structure may be automatically performed not only with respect to a single missing-tooth area but also with respect to all missing-tooth areas in the teeth image. As the implant structure is automatically placed on the basis of information on a relation with a surrounding structure of the missing-tooth area, the user does not need to adjust the implant structure in consideration of the surrounding structure even after the implant structure is placed, thereby increasing the user's convenience.

By presenting a simulation result to the user in consideration of the information on the relation with the surrounding structure of the missing-tooth area in which the implant structure is placed, the user may receive a guide at the time of an implant procedure. As the implant structure is automatically placed on the basis of the information on the relation with the surrounding structure of the missing-tooth area, anatomical knowledge about the surrounding structure is reflected, thereby improving accuracy thereof.

In addition, it is possible to provide a realistic simulation same as an actual procedure. For example, by providing a simulation in which a bridge is automatically generated according to the number of fixtures placed, it is possible to provide the user so that a simulation is performed such as a result after the actual procedure, thereby solving a problem such as low effectiveness occurring when only a simulation for a single crown is provided when consulting with a patient.

BEST MODE FOR CARRYING OUT THE INVENTION

Figure 1:
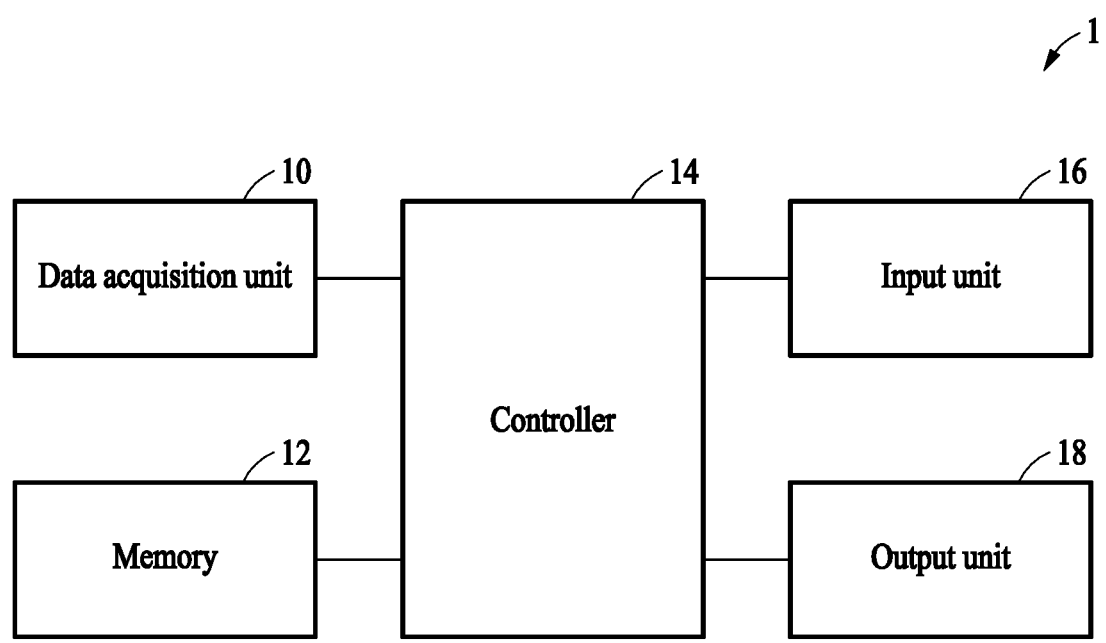
FIG. 1 is a diagram illustrating a configuration of a teeth image processing device according to an example embodiment.

The aspects and features of the present invention and methods for achieving the aspects and features will be apparent by referring to the example embodiments to be described in detail with reference to the accompanying drawings. However, the present invention is not limited to the example embodiments disclosed hereinafter, but can be implemented in various different forms. The example embodiments are merely provided so that the present invention is thorough and complete, and fully conveys the scope of the present invention to those skilled in the art, and the present invention is only defined within the scope of the appended claims. Throughout the entire specification, the same or like reference numerals designate the same or like elements.

In describing the example embodiments, a detailed description of related known configurations or functions incorporated herein will be omitted when it is determined that the detailed description thereof may unnecessarily obscure the subject matter of the present invention. The terms which will be described below are terms defined in consideration of the functions in the present invention, and may be different according to users, intentions of the users, or customs. Therefore, the definitions of the terms should be made based on the contents throughout the specification.

Combinations of blocks in the accompanying block diagrams or steps in the accompanying flowcharts can be executed by computer program instructions (execution engine), and the computer program instructions can be mounted in a processor of a general-use computer, special-use computer or other programmable data processing equipment. Thus, the instructions executed through the processor of the computer or other programmable data processing equipment generate units for performing functions described in the respective blocks of the block diagrams or the respective steps of the flowcharts.

The computer program instructions can be stored in a computer usable or readable memory oriented to a computer or other programmable data processing equipment, in order to implement functions in a specific method. Thus, the instructions stored in the computer usable or readable memory can be used to manufacture products including instruction units for performing the functions described in the respective blocks of the block diagrams or the respective steps of the flowcharts.

In addition, the computer program instructions can be mounted in the computer or other programmable data processing equipment. Therefore, instructions which generate processes by performing a series of operation steps on the computer or other programmable data processing equipment and operate the computer or other programmable data processing equipment can provide steps for executing the functions described in the respective blocks of the block diagrams and the respective steps of the flowcharts.

Each of the blocks or steps may indicate a part of a module, segment or code including one or more executable instructions for executing specific logical functions. In some substitutions, the functions described in the blocks or steps can be performed out of sequence. For example, two blocks or steps can be operated or performed substantially at the same time, and the blocks or steps can be operated or performed in a reverse order of the corresponding function.

Hereinafter, the example embodiments will be described in detail with reference to the accompanying drawings. However, the example embodiments may be modified in various different forms, and the scope of the present invention is not limited to the example embodiments described below. The example embodiments are provided to more completely describe the present invention to those skilled in the art.

FIG. 1 is a diagram illustrating a configuration of a teeth image processing device according to an example embodiment.

A teeth image processing device 1 is an electronic device capable of executing a medical image processing program such as a guide design program for dental implant surgery. The electronic device includes a computer, a notebook computer, a laptop computer, a tablet PC, a smart phone, a mobile phone, a personal media player (PMP), a personal digital assistant (PDA), and the like. The medical image processing program includes a scan program and a CAD program in addition to the guide design program. In addition, the medical image processing program may be applied to a program for processing a general medical image other than a program for dental implant surgery.

An image processing process using a teeth image processing program including the guide design program includes processes of registering a surgical patient, acquiring data of a CT image and an oral model image of the registered patient, matching the CT image and the oral model image, generating an arch line from the matched image data and generating a panoramic image using the arch line, determining a position and size of a crown model in the oral model image of the patient, determining a position of an implant structure including a fixture in the CT image of the patient, designing a guide shape, and outputting a final guide.

Among the above-described processes, the present invention relates to a process of automatically extracting a missing-tooth area through tooth segmentation, determining information on placement of an implant structure in the extracted missing-tooth area, and automatically placing the implant structure on a teeth image according to the determined information on the placement. The implant structure includes a fixture, a crown, and an abutment. The information on the placement includes a position, angle, height, width, length, diameter, shape, and the like of the fixture or crown.

Hereinafter, a configuration of the teeth image processing device 1 having the above-described features will be described with reference to the configuration of FIG. 1.

Referring to FIG. 1, the teeth image processing device 1 according to an example embodiment includes a data acquisition unit 10, a storage unit 12, a controller 14, an input unit 16, and an output unit 18.

The data acquisition unit 10 acquires teeth image data from a patient. The teeth image data required for placement of an implant structure includes a CT image, an oral model image, and the like. The data acquisition unit 10 may execute the CT image and the oral model image on a program or load data stored in a web page and a server.

The oral model image is image data having information on actual teeth including a damaged tooth. The oral model image may be obtained by scanning a plaster model generated by imitating a patient's oral cavity with a 3D scanner. As another example, the oral model image may be obtained by scanning the inside of the patient's oral cavity with a 3D intra-oral scanner. The acquired oral model image data may be stored in the storage unit 12.

The CT image may be acquired by generating tomographic images of the patient's head using a computed tomography (CT) or a cone beam (CB) CT, segmenting a boundary of a tooth part in each tomographic image, and then combining the images into one. The oral model images and CT image include an image obtained by imaging maxillary teeth under the maxillary teeth with the patient's mouth open, an image obtained by imaging mandibular teeth above the mandibular teeth with the patient's mouth open, and an image obtained by imaging a local area with the mouth closed, an oral radiograph, and the like. The acquired CT image data may be stored in the storage unit 12.

The storage unit 12 stores various pieces of data such as information required for performing an operation of the teeth image processing device 1 and information generated according to the operation performed. The storage unit 12 according to an example embodiment may store data of an oral model image and a CT image of an individual patient, and may provide, to the controller 14, an oral model image and a CT image of a specific patient from among the entire oral model images and CT images in response to a user's request at the time of dental treatment simulation. In this case, the storage unit 12 may store an image of upper teeth and an image of lower teeth of the individual patient, and may provide, to the controller 14, an image of upper teeth and an image of lower teeth matching an oral model image and a CT image of a specific patient in response to the user's request.

The controller 14 plans implant placement through control by a computer program and controls each component while performing a simulation on a teeth image according to an implant placement plan. The controller 14 configures screen information displayed on a screen through the output unit 18. The teeth image refers to a multidimensional image such as two-dimensional (2D), three-dimensional (3D), and the like showing arrangement of a patient's teeth generated for implant surgery planning. Various types of images such as an X-ray image, a CT image, an MRI image, a panoramic image, an oral scan image, an image generated through reconfiguration, and an image obtained by matching a plurality of images may be used for the implant surgery plan.

The controller 14 according to an example embodiment automatically places an implant structure according to a single placement mode or a multiple placement mode, with respect to a teeth image. The single placement mode is a mode for automatically placing an implant structure in a single missing-tooth area in the teeth image. The multiple placement mode is a mode for automatically placing an implant structure in all missing-tooth areas in the teeth image.

The controller 14 according to an example embodiment recognizes a missing-tooth area through tooth segmentation in the entered automatic placement mode. The missing-tooth area refers to an area that is extracted or damaged. In order to recognize the missing-tooth area, the controller 14 image-processes the teeth image. For example, a bone part is removed from the teeth image, and a tooth area is segmented in the teeth image from which the bone part is removed. Subsequently, a tooth number is designated to the segmented tooth area along a preset axial direction, and at least one missing-tooth area is extracted from the tooth area designated with the tooth number. An example embodiment thereof will be described later with reference to step 1 (teeth segmentation step) of FIG. 3.

The controller 14 according to an example embodiment determines information on placement of an implant structure to be actually placed according to an oral environment of a patient, and then automatically places and simulates the implant structure on the teeth image according to the determined information on the placement. The information on the placement includes a position, angle, height, width, length, diameter, shape, and the like of the implant structure. For example, the controller 14 analyzes, on the basis of the missing-tooth area, information relations with surrounding structures, such as a gingival bone, gingival margin, adjacent tooth, maxillary sinus, neural tube, bone density, and the like, and places the implant structure in the missing-tooth area by reflecting the analyzed information on the relations with the surrounding structures. As the implant structure is automatically placed on the basis of the information on the relations with the surrounding structures of the missing-tooth area, anatomical knowledge about the surrounding structures is reflected, thereby improving accuracy. An implant structure placing method of the controller 14 reflecting the information on the relations with the surrounding structures will be described later with reference to FIG. 3.

The controller 14 according to an example embodiment simultaneously performs simulations for a plurality of crowns. In this case, the controller 14 may automatically generate a bridge according to the number of fixtures placed. For example, when a middle fixture is deleted in a state in which three or more fixtures are successively placed in the teeth image, the controller 14 generates a bridge that connects crowns successively placed at positions corresponding to those of respective fixtures. An example embodiment thereof will be described later with reference to FIG. 7.

The input unit 16 receives a user operation signal. For example, the input unit 16 receives a user operation signal for entering an automatic placement mode including a single placement mode and a multiple placement mode. In order to enter the single placement mode, a selection signal for designating a predetermined missing-tooth area in the teeth image may be received. An example embodiment thereof will be described later with reference to FIG. 2. In order to enter the multiple placement mode, the selection signal may be received through a user interface for automatically placing implant structures with respect to all missing-tooth areas in the teeth image. An example embodiment thereof will be described later with reference to FIG. 4.

The input unit 16 receives a user operation for fine adjustment, if necessary, with respect to image data including a fixture, which is determined by the controller 14 and displayed on the screen through the output unit 18, to additionally adjust a position and size of the fixture.

The output unit 18 displays the screen. In this case, the output unit 18 displays image data (CT image, oral model image, panoramic image, and the like) on the screen. The CT image may be represented as an axial view, a sagittal view, a coronal view, or the like. In addition, the output unit 18 displays an implant structure placement result on an image in the screen and simulates the implant structure placement result. The output unit 18 displays an automatic placement mode screen. In order to enter a multi-mode for automatically placing implant structures with respect to all missing teeth in the teeth image, the output unit 18 may display a user interface for selecting the multiple placement mode on the screen.

Figure 2:
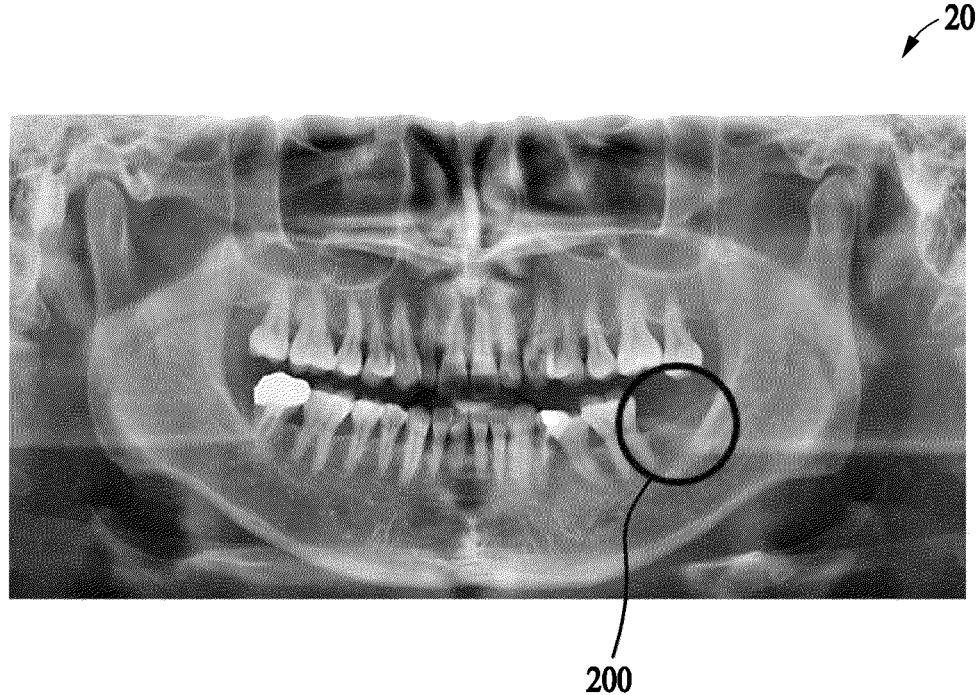
FIG. 2 is a diagram illustrating a single placement mode entry screen according to an example embodiment.

FIG. 2 is a diagram illustrating a single placement mode entry screen according to an example embodiment.

Referring to FIG. 2, the teeth image processing device enters a single placement mode by receiving, from a user, a selection signal for designating a predetermined missing-tooth area 200 in a teeth image, for example, a panoramic image 20. The single placement mode is a mode for automatically placing an implant structure with respect to a single missing-tooth area in the teeth image. The selection signal may be inputted through an operation of clicking a mouse with respect to the missing-tooth area 200. When entering the single placement mode, the teeth image processing device places an implant structure including a fixture, an abutment, a crown, and the like in the designated missing-tooth area. A process of automatically placing the implant structure in the single placement mode will be described with reference to FIG. 3 to be described later.

Figure 3:
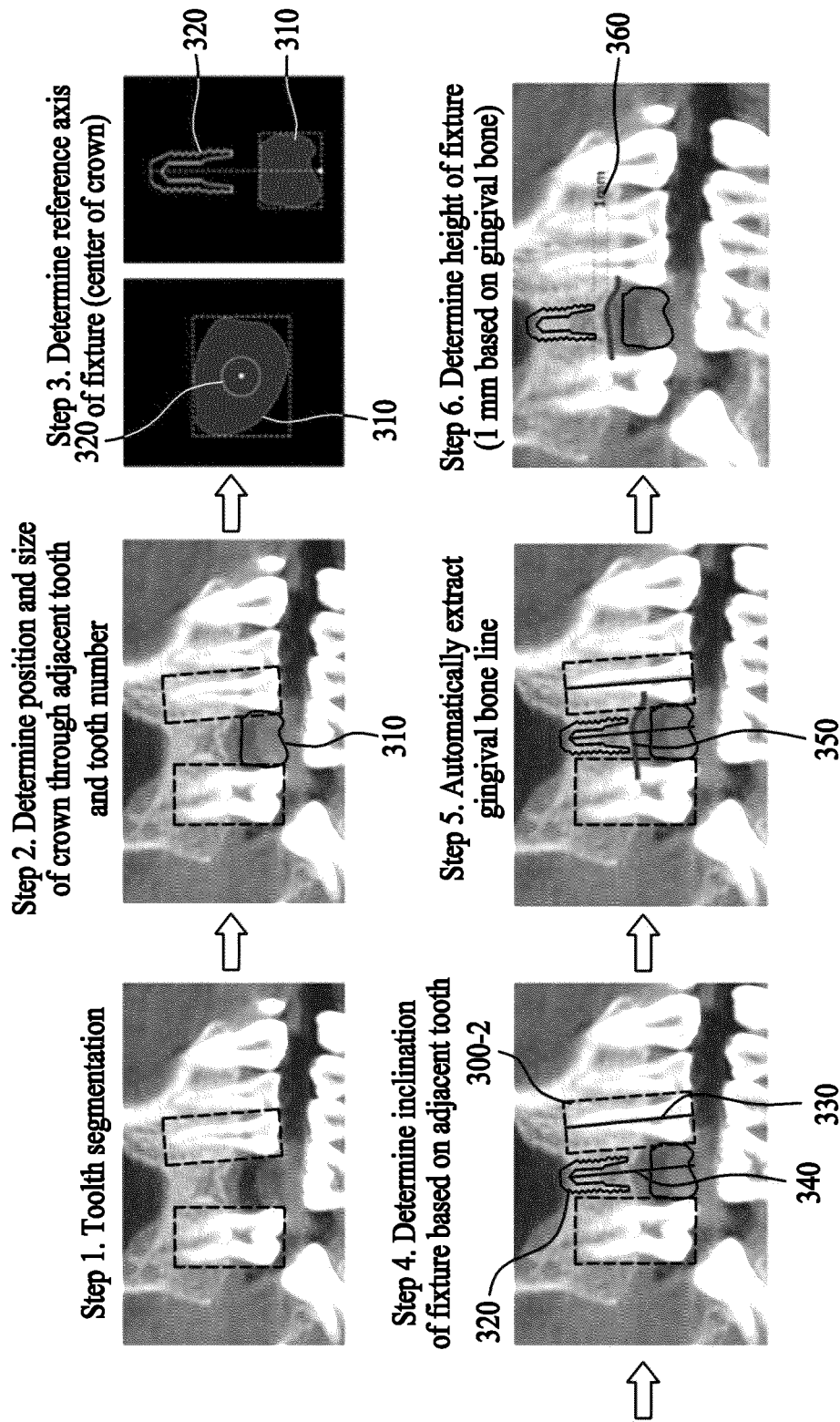
FIG. 3 is a diagram illustrating an image screen for showing a process of automatically placing an implant structure through a single placement mode according to an example embodiment.

FIG. 3 is a diagram illustrating an image screen for showing a process of automatically placing an implant structure through a single placement mode according to an example embodiment.

FIG. 3 illustrates a process of a single placement mode for automatically placing an implant structure with respect to a single missing-tooth area. However, it is noted that the same basis may be applied to a multiple placement mode for automatically placing implant structures in all missing-tooth areas.

In step 1, the teeth image processing device automatically segments a tooth area. To this end, after a bone part is removed from a CT image or a panoramic image, the tooth area is segmented in the CT image or the panoramic image from which the bone part is removed. In this case, it is possible to perform an operation of extracting a hard tissue area from a teeth image and removing the bone part from the extracted hard tissue area. For example, a hard tissue is extracted by removing soft tissue, air, water, and the like from the teeth image. The hard tissue includes teeth, a bone, an implant, and the like, and the bone includes a neck bone, a jaw bone, and the like. A bone density, gray scale, Hounsfield field unit (HU), and the like may be used to extract a soft tissue, a hard tissue, and a bone part in the hard tissue. Subsequently, each tooth area is segmented by setting a boundary for each individual tooth from which the bone part is removed.

Subsequently, a tooth number is designated to each segmented tooth area. For example, after a central point of each tooth area is selected, the tooth number is automatically set along a horizontal axis direction on the basis of the selected central point. The tooth number may be set using a federation dentaire internationale (FDI) numbering system. This method is an international notation widely used by dentists. Through the automatically set tooth number, an order and position of teeth in a row may be identified.

Furthermore, a missing-tooth area is automatically extracted from the segmented tooth area. For example, when a distance between central points of respective individual teeth for which tooth numbers are set exceeds a preset distance, a corresponding tooth is determined as a missing tooth. As another example, in a panoramic image, when a distance between a central point of each individual tooth for which a tooth number is set and an arch line exceeds a preset interval, a corresponding tooth is determined as a missing tooth. As a missing-tooth area is automatically extracted, an implant structure may be automatically placed with respect to all missing-tooth areas even when the user does not move to every single missing-tooth area and designate the missing-tooth area. From step 2, the implant structure is placed with respect to the missing-tooth area.

In step 2, the teeth image processing device places a crown 310 in the missing-tooth area. In this case, a placement position and size of the crown 310 may be determined. A shape of the crown 310 is automatically determined according to a tooth number of a missing tooth. In addition, on the basis of a result of analyzing a surrounding structure, the placement position and size of the crown 310 are adjusted. For example, a width of the crown 310 is determined according to a space of a missing-tooth area between adjacent teeth 300-1 and 300-2 for each designated tooth number, and a height of the crown 310 is determined according to an occlusal height of an antagonist tooth. The adjacent teeth 300-1 and 300-2 refer to teeth positioned on left and right sides of the missing tooth, and the antagonist tooth refer to a tooth formed at a maxillary or mandibular position corresponding to the missing tooth on the basis of tooth occlusion. The placement position of the crown 310 may be adjusted according to a position of the fixture 320. For example, the crown 310 is disposed at a preset distance on the basis of an upper end of the fixture, for example, at a position of 3 mm.

In step 3, the teeth image processing device determines an initial position of the fixture 320, using the position of the crown 310 disposed on the CT image or the panoramic image. For example, the initial position of the fixture 320 is determined on the basis of an axis of the crown 310. That is, the initial position of the fixture 320 is determined to be positioned at the center of the crown 310 while having a central axis same as a central axis of the crown 310. However, when a final position of the fixture 320 is determined in consideration of other anatomical structures including a gingival bone, the central axis of the crown 310 and the central axis of the fixture 320 may be different from each other. A diameter of the fixture may be adjusted according to the designated tooth number.

Subsequently, the placement position and size of the fixture 320 is adjusted on the basis of the result of analyzing the surrounding structure of the fixture 320 through steps 4 to 6. In step 4, the teeth image processing device may adjust a placement angle of the fixture 320 using an angle between the fixture 320 and the adjacent teeth 300-1 and 300-2 of a patient in the CT image or the panoramic image. For example, in the CT image or the panoramic image, an inclination 340 of the fixture 320 is determined so as to be parallel to an inclination 330 of the adjacent tooth 300-2 in a mesial direction. When there is no adjacent tooth, the inclination of the fixture 320 may be adjusted so as to be parallel to another tooth, for example, a placed fixture or a fixture to be placed. Furthermore, a length of the fixture 320 may be adjusted by reflecting a length of the adjacent tooth.

In steps 5 and 6, the teeth image processing device adjusts a position of the fixture in consideration of information on relations with surrounding structures, such as the gingival bone, cortical bone, adjacent tooth, adjacent fixture, and the like, on the basis of an initial position of a fixture placed for each tooth number. For example, the position of the fixture 320 is adjusted so that a distance between a gingival bone line 350 and the fixture 320 in a top direction of the fixture 320 is a preset distance, for example, at least 1 mm 360. The position of the fixture 320 is adjusted so that a distance between the fixture 320 and the gingival bone line 350 in a mesial direction is a preset distance, for example, at least 1.5 mm. To this end, for adjustment of the position of the fixture of step 6, a process of automatically extracting the gingival bone line 350 of step 5 may be preceded.

Furthermore, the position of the fixture 320 may be adjusted by reflecting a distance to the cortical bone, a distance to the adjacent tooth, and a distance between the fixtures. For example, in the case of a CBCT image, the position of the fixture 320 is adjusted so that the distance to cortical bone is a preset distance, for example, an interval of 1.5 mm. The position of the fixture 320 may be adjusted so that the distance to the adjacent tooth is a preset distance, for example, 1.5 to 2.0 mm. The position of the fixture 320 may be adjusted so that a distance to an adjacent fixture is a preset distance, for example, 3.0 mm.

Figure 4:
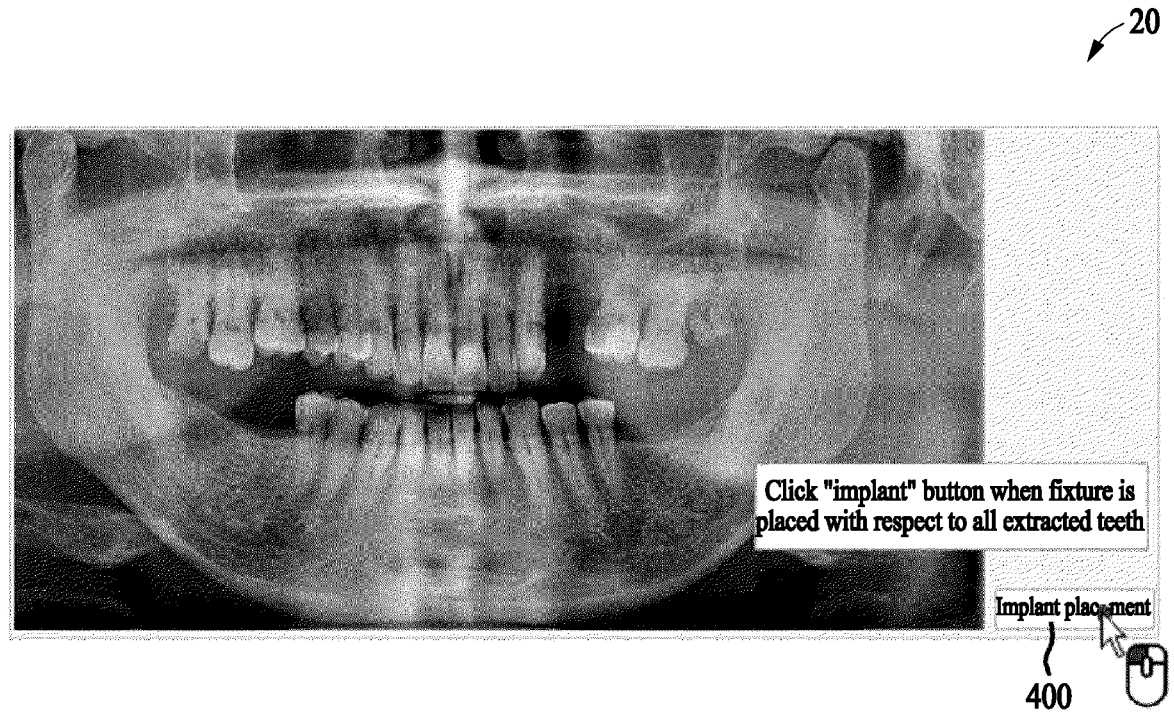
FIG. 4 is a diagram illustrating a multiple placement mode entry screen according to an example embodiment.

FIG. 4 is a diagram illustrating a multiple placement mode entry screen according to an example embodiment.

Referring to FIG. 4, in a teeth image, for example, a panoramic image 20, a teeth image processing device displays a user interface 400 for automatically placing fixtures with respect to all missing teeth in the teeth image on a screen. FIG. 4 illustrates an "implant placement button" as the user interface 400, however, the user interface is changeable to any existing interface form such as a context menu or the like that may be displayed as a graphic interface in addition to a button form.

When a selection signal for the user interface 400 is received from a user, the teeth image processing device receives enters a multiple placement mode. The multiple placement mode is a mode for automatically placing implant structures in all missing-tooth areas, respectively, in the teeth image. The selection signal may be inputted through an operation of clicking a mouse on the user interface 400. When entering the multiple placement mode, the teeth image processing device places the implant structures with respect to all missing-tooth areas. A basis for automatically placing the implant structures in all missing-tooth areas is the same as that of the single placement mode described above with reference to FIG. 3. All missing-tooth areas are automatically extracted through tooth segmentation of FIG. 3.

Figure 5:
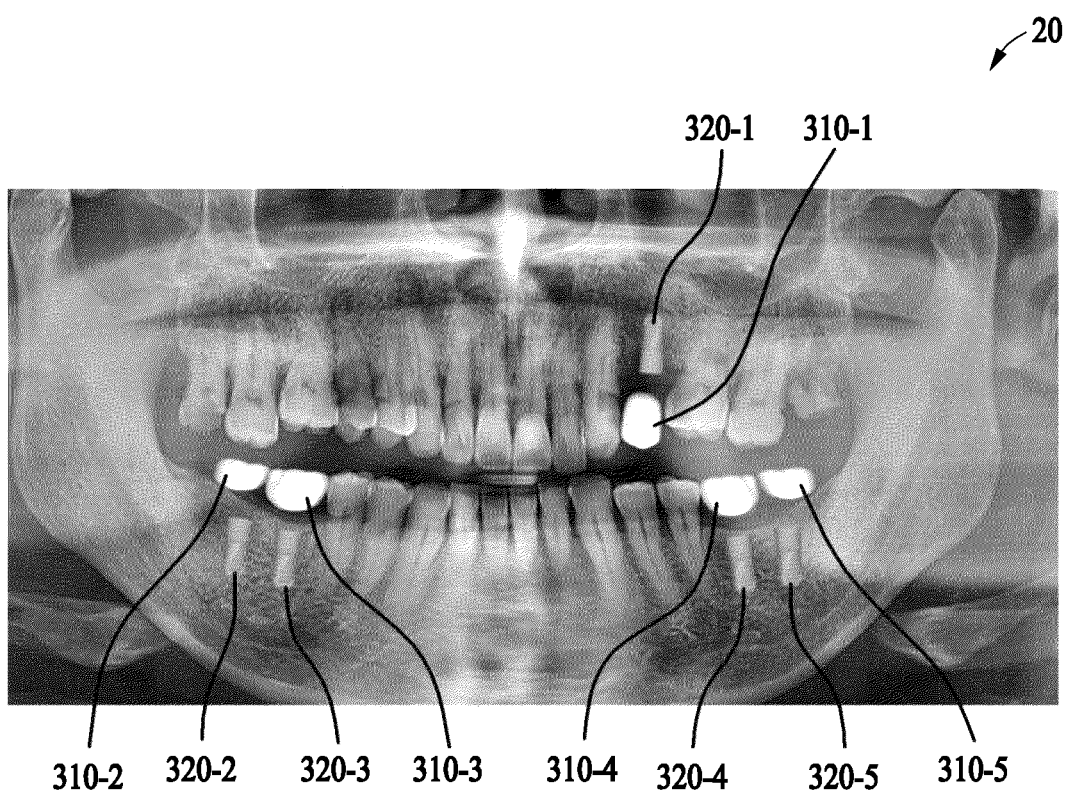
FIG. 5 is a diagram illustrating an image screen on which an implant structure is automatically placed in all missing-tooth areas through a multiple placement mode according to an example embodiment.

FIG. 5 is a diagram illustrating an image screen on which an implant structure is automatically placed in all missing-tooth areas through a multiple placement mode according to an example embodiment.

Referring to FIG. 5, when there are five missing-tooth areas in a teeth image, fixtures 320-1, 320-2, 320-3, 320-4, and 320-5 and crowns 310-1, 310-2, 310-3, 310-4, and 310-5 are automatically placed with respect to all missing-tooth areas in the multiple placement mode. The fixture placement of respective fixtures 320-1, 320-2, 320-3, 320-4, and 320-5 and crowns 310-1, 310-2, 310-3, 310-4, and 310-5 is performed on the same basis as the process of placing the implant structure in the single placement mode described above with reference to FIG. 3.

Figure 6:
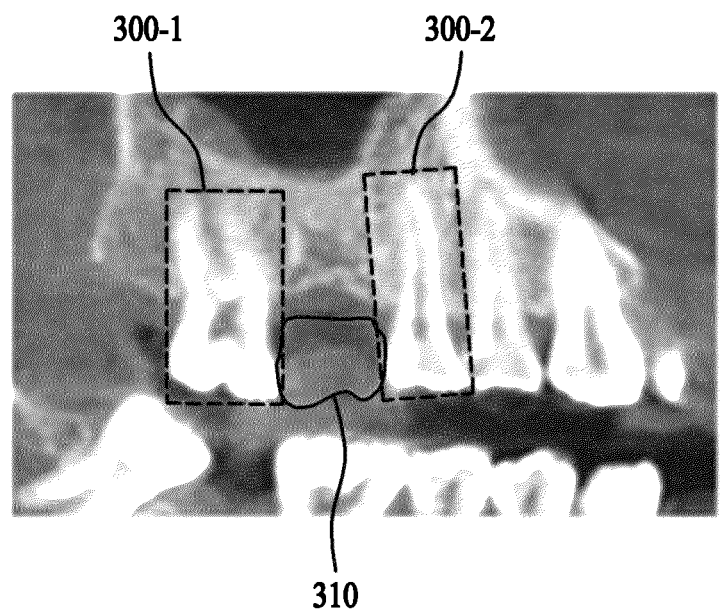
FIG. 6 is a diagram illustrating an image screen on which a crown is automatically placed according to an example embodiment.

FIG. 6 is a diagram illustrating an image screen on which a crown is automatically placed according to an example embodiment.

Referring to FIG. 6, a width of the crown 310 is determined according to a space of a missing-tooth area between the adjacent teeth 300-1 and 300-2 on the basis of the missing-tooth area, and a height of the crown 310 is determined according to an occlusal height of an antagonist tooth. When there is one or no adjacent tooth, the height of the crown may be determined in a ratio of other teeth (for example, a mirroring tooth of a missing tooth).

Figure 7:
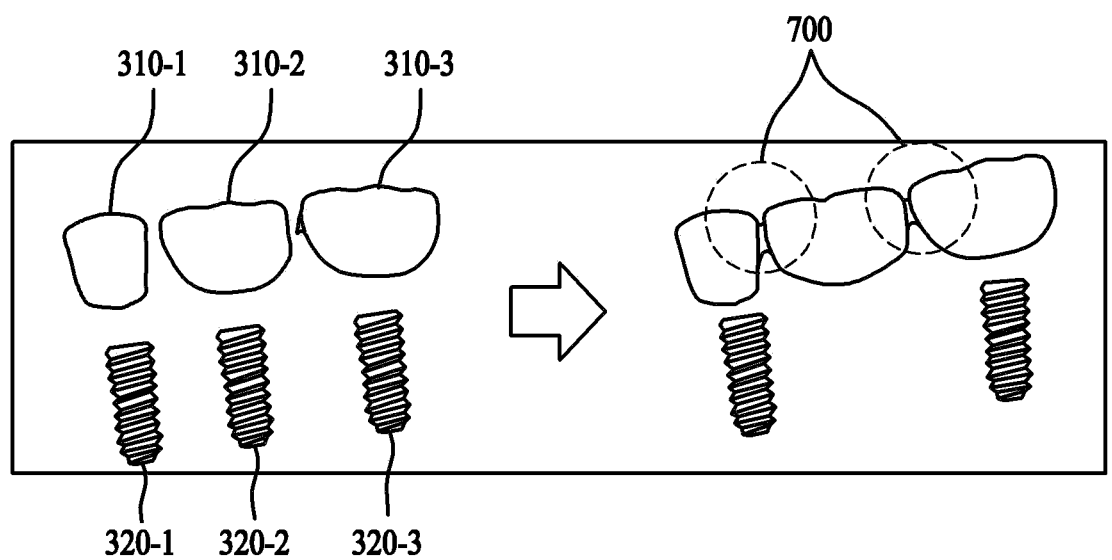
FIG. 7 is a diagram illustrating an image screen on which simulations for a plurality of crowns are provided according to an example embodiment.

FIG. 7 is a diagram illustrating an image screen on which simulations for a plurality of crowns are provided according to an example embodiment.

Referring to FIG. 7, a teeth image processing device may provide simulations for a plurality of crowns at the time of simulation. In this case, a bridge may be automatically generated according to the number of fixtures placed. For example, when the middle fixture 320-2 is deleted in a state in which three or more fixtures 320-1, 320-2, and 320-3 are successively placed in a teeth image, a bridge 700 that connects the crowns 310-1, 310-2, and 310-3 successively placed at positions corresponding to those of respective fixtures 320-1, 320-2, and 320-3 is automatically generated. Accordingly, it is possible to provide the same simulation as a result after an actual procedure.

Figure 8:
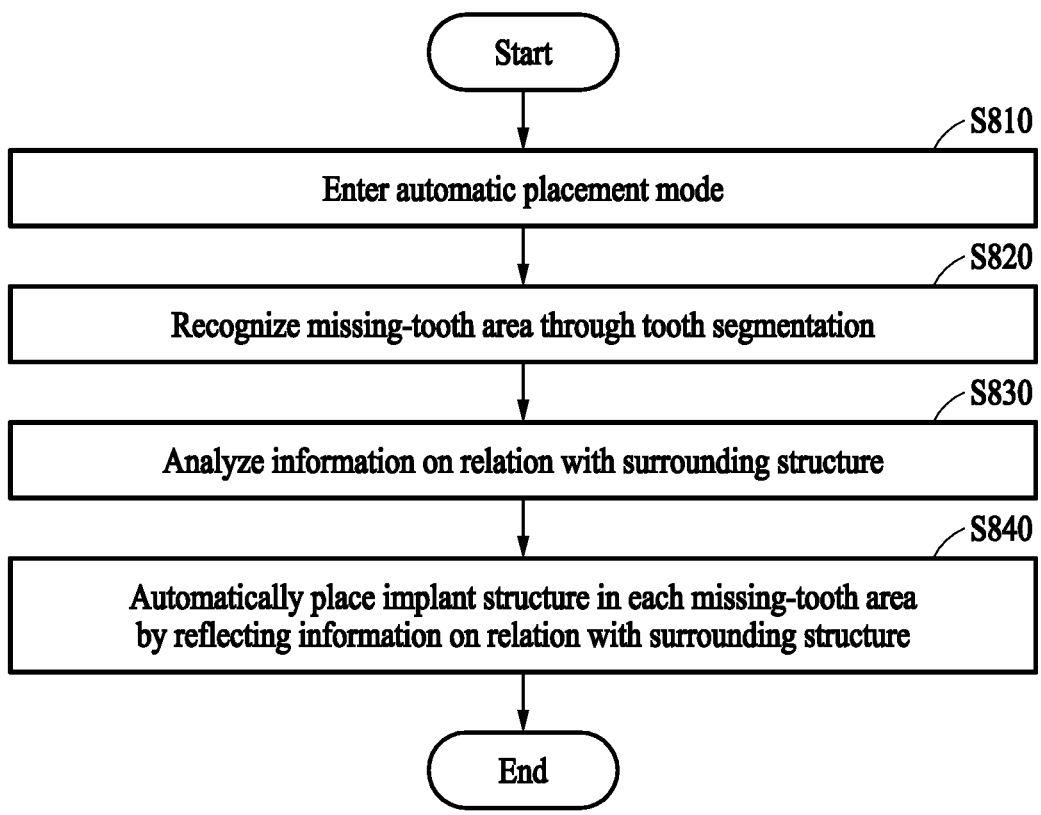
FIG. 8 is a diagram illustrating a flow of an implant surgery planning method according to an example embodiment.

FIG. 8 is a diagram illustrating a flow of an implant surgery planning method according to an example embodiment.

Referring to FIG. 8, a teeth image processing device enters a predetermined automatic placement mode, with respect to a teeth image, among a single placement mode and a multiple placement mode (S810). The single placement mode is a mode for automatically placing an implant structure with respect to a single missing-tooth area in the teeth image. The multiple placement mode is a mode for automatically placing implant structures with respect to all missing-tooth areas in the teeth image. The single placement mode may be entered by receiving a selection signal for designating a predetermined missing-tooth area in the teeth image. The multiple placement mode may be entered by receiving the selection signal through a user interface for automatically placing the implant structures with respect to all missing teeth in the teeth image.

Subsequently, the teeth image processing device recognizes at least one missing-tooth area through tooth segmentation in the entered automatic placement mode (S820). For example, a bone part is removed from the teeth image, and a tooth area is segmented in the teeth image from which the bone part is removed. In this case, after a tooth number is designated to the segmented tooth area along a preset axial direction, at least one missing-tooth area is extracted from the tooth area designated with the tooth number.

Subsequently, the teeth image processing device analyzes information on a relation with a surrounding structure on the basis of the recognized missing-tooth area (S830), and places the implant structure in the at least one missing-tooth area by reflecting the analyzed information on the relation with the surrounding structure (S840).

For example, when a fixture is placed, a diameter of the fixture may be determined according to the designated tooth number, and a length of the fixture may be determined by reflecting a length of an adjacent tooth on the basis of a missing-tooth area. In addition, an angle including an inclination of the fixture may be determined so as to be parallel to the adjacent tooth in a mesial direction on the basis of the missing-tooth area. A position of the fixture may be determined so that at least one of a distance to a gingival bone, a distance to a cortical bone, a distance to the adjacent tooth, and a distance between adjacent fixtures is a preset interval.

When a crown is placed, the crown may be disposed at a preset distance on the basis of an upper end of a fixture whose position is determined. A width of the crown may be determined according to a space of a missing-tooth area between adjacent teeth. A height of the crown may be determined according to an occlusal height of an antagonist tooth. When there is one or no adjacent tooth, the height of the crown may be determined in a ratio of other teeth.

Furthermore, a step of simultaneously performing simulations for a plurality of crowns may be further included. In this case, a bridge may be automatically generated according to the number of fixtures placed. For example, when a middle fixture is deleted in a state in which three or more fixtures are successively placed in a teeth image, a bridge is generated that connects crowns successively placed at positions corresponding to those of respective fixtures. Accordingly, it is possible to provide the same simulation result as an actual procedure.

While the present invention includes example embodiments, it will be apparent to one of ordinary skill in the art that various changes in form and details may be made in these example embodiments without departing from the spirit and scope of the claims and their equivalents. The example embodiments described herein are to be considered in a descriptive sense only, and not for purposes of limitation. Therefore, the scope of the present invention is defined not by the detailed description, but by the claims and their equivalents, and all variations within the scope of the claims and their equivalents are to be construed as being included in the present invention.

The invention claimed is:

1. An implant surgery planning method comprising:
    entering a predetermined automatic placement mode, with respect to a teeth image, among a single placement mode for automatically placing an implant structure with respect to a single missing-tooth area in the teeth image and a multiple placement mode for automatically placing the implant structure with respect to all missing-tooth areas in the teeth image;
recognizing at least one missing-tooth area through tooth segmentation in the entered automatic placement mode;
analyzing information on a relation with a surrounding structure on the basis of the recognized missing-tooth area; and
automatically placing the implant structure in the at least one missing-tooth area based on information on placement that reflected the analyzed information on the relation with the surrounding structure.

2. The implant surgery planning method of claim 1, wherein the entering of the predetermined automatic placement mode comprises:
entering a single placement mode by receiving a selection signal for designating a predetermined missing-tooth area in the teeth image; and
entering a multiple placement mode by receiving the selection signal through a user interface for automatically placing implant structures with respect to all missing teeth in the teeth image.

3. The implant surgery planning method of claim 1, wherein the recognizing of the at least one missing-tooth area comprises:
removing a bone part from the teeth image;
segmenting a tooth area in the teeth image from which the bone part is removed;
designating a tooth number to the segmented tooth area along a preset axial direction; and
extracting the at least one missing-tooth area from the tooth area designated with the tooth number.

4. The implant surgery planning method of claim 1, wherein the automatically placing of the implant structure comprises:
determining a diameter of a fixture according to a designated tooth number;
determining a length of the fixture by reflecting a length of an adjacent tooth on the basis of the missing-tooth area;
determining an angle including an inclination of the fixture so as to be parallel to the adjacent tooth in a mesial direction on the basis of the missing-tooth area; and
determining a position of the fixture so that at least one of a distance to a gingival bone, a distance to a cortical bone, a distance to the adjacent tooth, and a distance between adjacent fixtures is a preset interval.

5. The implant surgery planning method of claim 1, wherein the automatically placing of the implant structure comprises:
disposing a crown at a predetermined distance on the basis of an upper end of a fixture whose position is determined;
determining a width of the crown according to a space of a missing-tooth area between adjacent teeth;
determining a height of the crown according to an occlusal height of an antagonist tooth; and
determining the height of the crown in a ratio of other teeth when there is one or no adjacent tooth.

6. The implant surgery planning method of claim 1, further comprising:
simultaneously performing simulations for a plurality of crowns.

7. The implant surgery planning method of claim 6, wherein the simultaneously performing of the simulations for the plurality of crowns comprises:
automatically generating a bridge according to the number of fixtures placed, and generating a bridge that connects crowns successively placed at positions corresponding to those of respective fixtures when a middle fixture is deleted in a state in which three or more fixtures are successively placed in the teeth image.

8. A user interface providing method for implant surgery planning, the method comprising:
displaying a teeth image;
displaying a user interface for placing an implant structure with respect to all missing teeth in the teeth image;
entering a single placement mode when a selection signal for designating a predetermined missing-tooth area in the teeth image is received, automatically placing the implant structure in the designated missing-tooth area, and displaying the placed implant structure on a screen; and
entering a multiple placement mode when a selection signal for the user interface is received, automatically placing the implant structure in all missing-tooth areas, and displaying the placed implant structure on the screen.

9. A teeth image processing device comprising:
a data acquisition unit configured to acquire teeth image data;
a controller configured to automatically place and simulate an implant structure in at least one missing-tooth area by configuring a screen for performing a single placement mode and a multiple placement mode with respect to an acquired teeth image, analyzing information on a relation with a surrounding structure on the basis of the missing-tooth area, and determining information on placement by reflecting the analyzed information on the relation with the surrounding structure;
an input unit configured to receive an operation signal for entering a predetermined automatic placement mode; and
an output unit configured to display an automatic placement mode screen, and display a placement result on the teeth image.

10. The teeth image processing device of claim 9, wherein
the output unit is configured to display a user interface for entering the multiple placement mode on the screen, and
the controller is configured to:
enter the single placement mode when a selection signal for designating a predetermined missing-tooth area in the teeth image is received from the input unit, and automatically place the implant structure in the designated missing-tooth area; and
enter the multiple placement mode when a selection signal for the user interface for entering the multiple placement mode is received from the input unit, and automatically place the implant structure in all missing-tooth areas.

11. The teeth image processing device of claim 9, wherein the controller is configured to:
perform image processing to remove a bone part from the teeth image and segment a tooth area in the teeth image from which the bone part is removed;
designate a tooth number to the segmented tooth area along a preset axial direction; and
extract at least one missing-tooth area from the tooth area designated with the tooth number.

12. The teeth image processing device of claim 9, wherein the controller is configured to:

determine a diameter of a fixture according to a designated tooth number;

determine a length of the fixture by reflecting a length of an adjacent tooth on the basis of the missing-tooth area;

determine an angle including an inclination of the fixture so as to be parallel to the adjacent tooth in a mesial direction on the basis of the missing-tooth area; and determine a position of the fixture so that at least one of a distance to a gingival bone, a distance to a cortical bone, a distance to the adjacent tooth, and a distance between adjacent fixtures is a preset interval.

13. The teeth image processing device of claim 9, wherein the controller is configured to:

dispose a crown at a predetermined distance on the basis of an upper end of a fixture whose position is determined;

determine a width of the crown according to a space of a missing-tooth area between adjacent teeth;

determine a height of the crown according to an occlusal height of an antagonist tooth; and determine the height of the crown in a ratio of other teeth when there is one or no adjacent tooth.

14. The teeth image processing device of claim 9, wherein the controller is configured to simultaneously perform simulations for a plurality of crowns.

15. The teeth image processing device of claim 14, wherein the controller is configured to automatically generate a bridge according to the number of fixtures placed, and generate a bridge that connects crowns successively placed at positions corresponding to those of respective fixtures when a middle fixture is deleted in a state in which three or more fixtures are successively placed in the teeth image.

\* \* \* \* \*